United States Patent [19]

Maurukas

[11] 4,218,536

[45] Aug. 19, 1980

[54] PROCESS-STABLE CO-ENZYME NAD SOLUTION

[76] Inventor: Jonas Maurukas, 6823 Lake Ave., Elyria, Ohio 44035

[21] Appl. No.: 948,146

[22] Filed: Oct. 3, 1978

[51] Int. Cl.$^2$ .................. C09K 3/00; G01N 31/06; G01N 31/14; G01N 33/16
[52] U.S. Cl. ............................. 435/14; 435/26; 23/230 B; 252/408
[58] Field of Search ........... 195/99, 103.5 R, 103.5 C, 195/63, 68; 252/408; 23/230 B; 435/14, 26, 195–199, 103.5 R, 103.5 C, 63, 68

[56] References Cited

U.S. PATENT DOCUMENTS

| | | | |
|---|---|---|---|
| 3,764,478 | 10/1973 | Bergmeyer et al. | 195/99 |
| 3,776,900 | 12/1973 | Hammer | 195/99 |
| 3,819,487 | 6/1974 | Bernt et al. | 195/99 |
| 3,876,375 | 4/1975 | Maururas | 252/408 |
| 4,097,338 | 6/1978 | Konttinen et al. | 195/103.5 R |
| 4,111,752 | 9/1978 | Weetall | 195/103.5 R |
| 4,121,905 | 10/1978 | Maurukas | 252/408 |
| 4,153,511 | 5/1979 | Modrovich | 195/99 |

FOREIGN PATENT DOCUMENTS 7603588  10/1976  Netherlands ................. 195/99

OTHER PUBLICATIONS

Gallati, H., J. Clin. Chem. Clin. Biochem., vol. 14, pp. 9–13, (1976).

*Primary Examiner*—Teddy S. Gron

[57] ABSTRACT

A stable oxidized co-enzyme NAD reagent, ready for use in photometric assay of body fluids is prepared by dissolving the co-enzyme NAD in a neutral organic solvent such as glycol (antifreeze). The product is a liquid, easily measured by volume for carrying out analytical operation, and can be stored in liquid condition at low temperatures (0° C. to −20° C.) without freezing and thawing.

8 Claims, No Drawings

PROCESS-STABLE CO-ENZYME NAD SOLUTION

BACKGROUND

Nicotinamid adenine dinucleotides exist in two forms, both of which are used in assaying biological materials. The reduced or hydrogenated form is known as NADH, and the oxidized or dehydrogenated form used in this invention is known as NAD.

Both NAD and NADH are unstable and deteriorate rapidly if kept in the presence of water under ordinary conditions. Consequently, it has been the practice until recently to keep such materials in the absence of water, in a completely dry solid condition.

It is now known that NADH can be kept at room temperature without deterioration if the pure material is dissolved in essentially anhydrous glycol, especially if a small amount of an amine or other alkaline material is present. However NAD is not sufficiently stable if treated in the same manner, particularly not if kept alkaline.

SUMMARY OF THE INVENTION

I have discovered that NAD, the oxidized form of nicotinamid adenine dinucleotides, can be kept almost indefinitely without significant deterioration, if dissolved in ethylene glycol or other liquid polyol, and stored at a sufficiently low temperature.

The NAD solution so prepared can be supplied in bulk, at a known concentration, and can be diluted to a predetermined level for use in analytical procedures in a precise manner, by simple volumetric measurements which are quick and therefore very economical.

The unused stock solution, after removal of the quantity immediately needed, can be returned promptly to cold storage, and preserved unchanged until more of the reagent is needed.

THE PROBLEM

In the diagnosis of certain pathological conditions, it is frequently valuable to know the amount of activity or the quantity of certain substances present in a specimen of a biological fluid or tissue. One of the more effective means that has been proposed for making assays of such specimens is to provide a liquid reagent which contains one or more biological components reactive with a component of the specimen. Any given reagent is mixed with the specimen; the components are effective to cause an enzymatic reaction that involves the unknown substance. By observing this reaction, it is possible to determine the quantity or the amount of the activity of the unknown originally present.

Since such reagents contain one or more biological components such as enzymes, co-enzymes, or biological substrates, the reagents have inherently been very unstable in nature and have a very short shelf life. To insure the reagent being at optimum strength, it must be prepared at or immediately prior to the time the assay is made. The various components for the working reagent are prepared in solution in separate containers and maintained separated from each other. After all of the various components have been prepared, the appropriate quantities of each are combined to form the working reagent. A predetermined quantity of working reagent is then mixed with the specimen to produce the desired assay reactions. It may thus be seen that the accuracy of the assay is dependent upon the skill of the operator and the accuracy with which he prepares and uses the reagent. It can be readily appreciated that the foregoing process is very time consuming. The reagents of the above mentioned compositions are quite unstable and rapidly lose their activity. Consequently, if the reagent is not used within a matter of a few hours following its preparation, it must be discarded and therefore wasted.

It is an object of the present invention to provide means which will be effective to overcome the foregoing difficulties. More particularly, it is proposed to provide a novel assay material useful in making biological assays and a method for preparing the material. The assay material of this invention is in a liquid and stable state and may be easily handled and used, and will have a long shelf life.

The invention sought to be patented resides in the concept of preparing an improved stable liquid assay working reagent useful in the clinical diagnosis of pathological conditions.

Analyses of blood serum and other biologically active and biologically significant body fluids for enzyme and other critical components are commonly carried out by photometric procedures, which may be carried out in automated equipment, requiring supply of reagent consisting of standardized normal enzyme co-factor and particularly NAD which consists of nicotinamideadenine dinucleotide.

The co-factor NAD is commercially obtainable in oxidized or reduced form, but in this invention it is used in the oxidized form. In particular, NAD, in the presence of water, undergoes hydrolysis and leads to false analytical results. The consequence has been that working solutions of such co-enzyme in water have to be freshly prepared at the time of use by highly skilled personnel, which greatly increases the cost of the analysis. (R. J. Henry, D. Cannon, J. Winkleman, *Clinical Chemistry, Principles and Techniques* (New York: Harper & Row, Hoeber Medical Division, 2nd edition, 1974), p. 825). "Lactic Acid, NAD reagent should be freshly prepared and kept in refrigerator or on ice at all times, prepared everyday".

Amadore et al., *Clinical Chemistry* (Vol. 9) pgs. 391-399, 1963. This reference teaches the preparation of NAD in phosphate buffer with lactate at pH 8.8. To stabilize this preparation, for other than same day use one has to keep it frozen in a solid state at $-20°$ C.

Customarily NAD is supplied to medical laboratories in dry form. When dissolved in buffers or substrate, in preparation for diagnostic use, its useful life is short and fresh solution has to be prepared daily, or kept frozen in a solid state. The prior art shows that the problem has been known for a long time. No better art has been known than the time-consuming wasteful daily preparation of fresh solution of NAD.

"Aqueous solution at slightly acid pH is moderately stable, e.g. 1% solution keeps for about one week at 4° C. Above pH of 7, the rate of decomposition increases with pH." (Begmeyer, *Methods of Enzymatic Analysis,* Acad. Press Inc., N.Y. (1974), p. 545).

It has previously been proposed to avoid various problems resulting from use of water as a solvent by using organic solvents such as ethylene glycol. It has thus been proposed in my U.S. Pat. No. 3,876,375 to replace part of the water by glycol in certain biological preparations such as reference standard serums, so as to permit the storage in liquid state at low temperature such as $-20°$ C. without danger of deterioration resulting from freezing and thawing. In my U.S. Pat. No.

4,121,905, I proposed to reconstitute freezedried standardized human serum "for in vitro diagnosis" with 33% ethylene glycol, so as to extend useful shelf life of the reference control.

It is known that reduced co-enzyme NADH can be stabilized by dissolving it in anhydrous ethylene glycol, containing diethylamine or other mild base.

However, it has not been known that the extremely sensitive NAD could be easily prepared in a convenient and stable liquid form without any observable change in any of its properties.

DETAILED DISCLOSURE

In accordance with this invention; sensitive biological material and particularly beta-nicotinamide adenine dinucleotide (commonly called Co-enzyme 1, or when in its oxidized form is called NAD) is prepared in a stable liquid form which can be stored without change for long periods of time at low temperatures and can be used in analytical procedures with the same ease and with the same accuracy as freshly prepared working reagent.

Beta-nicotinamide adenine dinucleotide, oxidized form, called NAD, which is commercially available in dry form as disodium salt, is made up to a working solution, in accordance with this invention by dissolving it in one of the liquid polyols or a mixture of them, but preferably in anhydrous glycol.

The polyol may be ordinary glycol which is sometimes called ethylene glycol or may be propylene glycol or even butylene glycol, but ordinary ethylene glycol is preferred because of its considerably lower viscosity than the alternatives. This feature of ethylene glycol is extremely important because working solution is measured by pipettes and the viscosity of ethylene glycol is lower than that of the other mentioned glycols.

The concentration of the solution of the NAD in glycol or other polyol may be almost any convenient small value. A very dilute solution is most convenient, since it facilitates precise measurement of the required small quantity of the working reagent by means of a pipette. From about 0.1% to 10% will generally be suitable. SPECIFIC EXAMPLE:

A working solution of NAD of approximately 1.5% concentration (actually 1.5 grams per 100 ml) is prepared as follows:

1.5 grams of good quality of beta-nicotinamide adenine denucleotide NAD disodium salt is dissolved in 100 ml of anhydrous ethylene glycol.

This solution can be used for 6 months if it is kept at 5° C. temperature of household refrigerator or for 2 years if kept in a liquid state from about −12° to about −20° C. temperature of the freezer compartment of a household refrigerator.

This working solution can be used, for example, for measuring the serum or plasma glucose level of a blood sample, using the following additional reagents: 1000 ml of substrate prepared in water containing the following components: 0.4 micro-moles ATP (adenosine triphosphate), 1000 international units Glucose-6-phosphate dehydrogenase, 1000 I.U. Hexokinase, 100 micro-moles tris-buffer (tris-hydroxymethylaminomethane) adjusted to pH 7.8.

Any instrument capable of reading absorbance accurately with the sensitivety of 0.001 absorbance at 340 mu may be used.

(1) In 1 cm diameter cuvette, place and mix 2.9 ml of glucose substrate described above and 0.1 ml of stabilized NAD working reagent prepared in glycol.

(2) Place the cuvette into the ultraviolet spectrophotometer. Read and record the initial absorbance at 340 mu.

(3) Add 20 micro-liters of serum sample to reagent and mix.

(4) After 3 minutes read and record the final absorbance at 340 mu.

NOTE: A sample blank must be determined with all samples for greater accuracy.

Glucose concentration in milligrams per 100 ml is given by the formula: Delta absorbance=delta absorbance final−delta absorbance initial.

$\Delta A = \Delta A_{final} - \Delta A_{initial}$ mg% glucose $= \Delta A \times 440$ The factor 440 is derived from molar extinction coefficient of coenzyme NAD.

Results using a year old NAD reagent of this invention prepared as described above are at least as accurate as results obtained using freshly prepared NAD solution in buffer or in substrate.

In the foregoing example, detailed instructions are given for the determination of serum glucose. However, the same stock NAD in glycol can be used in other determinations, such as determining serum lactic dehydrogenase (LDH) and serum creatine phosphokinase (CPK) simply by adding the polyol solution to the substrate or to the buffer solution of the corresponding test.

When properly prepared and stored, this invention eliminates the cause for erroneous analytical reports, which can result from using aqueous solution of partially decomposed NAD and lead to a false diagnosis.

While the invention has been described above as involving solution of a specific material, NAD or co-enzyme 1 in essentially anhydrous polyol, for use in measuring the quantity of a particular enzyme present in human body fluid; it can also be used for other similar purposes, involving the enzymes including those from other living organisms and particularly animals such as when testing for abnormal conditions in cattle or other domestic animals.

What is claimed is:

1. A solution of oxidized co-enzyme NAD stored for at least one day prior to use for use in assaying enzymes present in body fluids, said solution consisting essentially of oxidized co-enzyme NAD dissolved in a substantially anhydrous solvent of the class consisting of liquid polyols and mixtures of them, characterized in that the solution had been stored for essentially the entire time since its preparation at a temperature in the range of about 4° to −20° C.

2. A solution as in claim 1 wherein the solvent is ethylene glycol.

3. A solution as in claim 1 wherein the solvent is propylene glycol.

4. A solution as in claim 1 wherein the solvent is glycerol.

5. A solution as in claim 1 wherein the solvent is butylene glycol.

6. A solution as in claim 1 wherein the solvent is pentane diol.

7. In a process for performing spectrophotometric assays of serum glucose on unknown naturally occuring whole blood, using NAD as a reagent the improvement which comprises employing the previously stored and stabilized liquid co-enzyme NAD composition of claim 1 as working reagent in conducting the spectrophotometric determination of said glucose.

8. A process as in claim 7 in which the co-enzyme NAD is employed as a solution in ethylene glycol.

* * * * *